(12) United States Patent  (10) Patent No.: US 7,455,737 B2
Boismier et al.  (45) Date of Patent: Nov. 25, 2008

(54) SELECTIVE TREATMENT OF LINEAR ELASTIC MATERIALS TO PRODUCE LOCALIZED AREAS OF SUPERELASTICITY

(75) Inventors: Dennis A. Boismier, Shorewood, MN (US); Justin M. Crank, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 341 days.

(21) Appl. No.: 10/647,619

(22) Filed: Aug. 25, 2003

(65) Prior Publication Data

US 2005/0049690 A1 Mar. 3, 2005

(51) Int. Cl.
*A61M 29/00* (2006.01)
(52) U.S. Cl. .................. 148/402; 148/902; 606/200; 623/1.18
(58) Field of Classification Search .............. 148/402, 148/902; 623/1.18, 1.19, 924
See application file for complete search history.

(56) References Cited

U.S. PATENT DOCUMENTS

| | | | |
|---|---|---|---|
| 3,174,851 A | 3/1965 | Buehler et al. | |
| 3,948,688 A | 4/1976 | Clark | |
| 4,283,233 A | 8/1981 | Goldstein et al. | |
| 4,435,229 A | 3/1984 | Johnson | |
| 4,484,955 A | 11/1984 | Hochstein | |
| 4,505,767 A | 3/1985 | Quin | |
| 4,654,092 A | 3/1987 | Melton | |
| 4,894,100 A | 1/1990 | Yamauchi et al. | |
| 4,935,068 A | 6/1990 | Duerig | |
| 4,943,326 A | 7/1990 | Ozawa et al. | |
| 5,066,341 A | 11/1991 | Grenouillet | |
| 5,069,226 A | 12/1991 | Yamauchi et al. | |
| 5,171,383 A | 12/1992 | Sagaye et al. | |
| 5,230,348 A | 7/1993 | Ishibe et al. | |
| 5,238,004 A | 8/1993 | Sahatjian et al. | |
| 5,341,818 A | 8/1994 | Abrams et al. | |
| 5,624,508 A | 4/1997 | Flomenblit et al. | |
| 5,637,089 A | 6/1997 | Abrams et al. | |
| 5,641,364 A | 6/1997 | Golberg et al. | |
| 5,683,245 A | 11/1997 | Sachdeva et al. | |
| 5,725,570 A * | 3/1998 | Heath ...................... 623/1.2 | |
| 5,776,162 A * | 7/1998 | Kleshinski ............... 623/1.18 | |
| 5,822,444 A | 10/1998 | Oizumi et al. | |
| 5,836,969 A * | 11/1998 | Kim et al. ................ 606/200 | |
| 5,958,159 A | 9/1999 | Prandi | |
| RE36,628 E * | 3/2000 | Sagae et al. ............. 148/537 | |
| 6,042,553 A | 3/2000 | Solar et al. | |

(Continued)

FOREIGN PATENT DOCUMENTS

EP 0 395 098 A1 10/1990

(Continued)

*Primary Examiner*—George Wyszomierski
(74) *Attorney, Agent, or Firm*—Crompton, Seager & Tuft LLC (57) ABSTRACT

Methods of selectively treating linear elastic materials to produce localized areas of superelasticity and/or shape-memory are disclosed. In an illustrative method, a linear elastic workpiece may be formed into a particular shape by cold-forming or other low-temperature process, and incorporated into a medical device such as an embolic protection filter, vena cava filter, stent or guidewire. A heat source may be used to apply thermal energy to selective areas of the workpiece, imparting superelasticity to the material.

6 Claims, 6 Drawing Sheets

U.S. PATENT DOCUMENTS

| | | | |
|---|---|---|---|
| 6,106,642 A | 8/2000 | DiCarlo et al. | |
| 6,149,742 A | 11/2000 | Carpenter et al. | |
| 6,217,567 B1 | 4/2001 | Zadno-Azizi et al. | |
| 6,254,550 B1 * | 7/2001 | McNamara et al. | 600/585 |
| 6,280,539 B1 | 8/2001 | Abrams et al. | |
| 6,306,105 B1 | 10/2001 | Rooney et al. | |
| 6,375,458 B1 | 4/2002 | Moorleghem et al. | |
| 6,375,629 B1 * | 4/2002 | Muni et al. | 600/585 |
| 6,451,052 B1 | 9/2002 | Burmeister et al. | |
| 6,485,507 B1 | 11/2002 | Walak et al. | |
| 6,540,849 B2 | 4/2003 | DiCarlo et al. | |
| 6,551,341 B2 * | 4/2003 | Boylan et al. | 606/200 |
| 6,582,461 B1 | 6/2003 | Burmeister et al. | |
| 6,585,753 B2 * | 7/2003 | Eder et al. | 623/1.15 |
| 6,669,794 B1 * | 12/2003 | Bellouard et al. | 148/563 |
| 2004/0111044 A1 * | 6/2004 | Davis et al. | 600/585 |

FOREIGN PATENT DOCUMENTS

JP    2003247053    5/2003

* cited by examiner

SELECTIVE TREATMENT OF LINEAR ELASTIC MATERIALS TO PRODUCE LOCALIZED AREAS OF SUPERELASTICITY

FIELD OF THE INVENTION

The present invention relates generally to the field of medical devices and methods of manufacturing medical devices. More specifically, the present invention relates to methods of selectively treating linear elastic materials to produce localized areas of superelasticity.

BACKGROUND OF THE INVENTION

Medical devices such as intravascular filters, guidewires, catheters, needles, needle stylets, and stents are used in performing a wide variety of medical procedures within the body. Such devices are typically formed from a number of components each exhibiting a differing performance characteristic within the body. In some medical applications, it may be desirable to alter the flexibility characteristics of certain components to improve the function of the device within the body. In the field of embolic protection filters, for example, it may be desirable to form a filter having specifically defined areas of flexibility to facilitate placement and/or removal of the device within the body. To impart such flexibility, some devices require additional manufacturing steps be taken to alter the dimensions or composition of the various components. In some cases, multiple components or materials are employed to impart flexibility to the device, requiring the use of additional joining processes such as soldering or bonding to assemble the components together.

More recent trends in the art have focused on the use of shape-memory alloys (SMA) and superelastic alloys to impart flexibility. Depending on the particular method of manufacturing, materials such as nickel-titanium alloy (Nitinol) have the ability to return to a particular shape upon a temperature-induced phase transformation, or exhibit superelasticity when subjected to a stress-induced phase transformation. In contrast to more conventional metals such as stainless steel, shape-memory and superelastic alloys are able to endure greater strains before plastically deforming, allowing the material to be used in applications demanding greater flexibility and torqueability.

Linear elastic materials are typically formed of superelastic alloys that have been specially treated to maintain a linear stress-strain response. Although similar in chemical composition to their superelastic counterparts, linear elastic materials do not exhibit the flat stress-strain plateau generally associated with superelastic materials. Instead, as recoverable strain increases, the stress in the material continues to increase linearly until plastic (i.e. permanent) deformation is achieved. As a result, such materials tend to be axially and torsionally stiffer than superelastic materials at higher deformations.

While shape-memory and superelastic alloys have widespread applications in the medical industry, the manufacturing and processing steps required to incorporate such materials into medical devices have proven difficult. Nickel-titanium alloys are often difficult to solder or braze to other materials, due to the formation of $TiO_2$ and other titanium oxides. Welding is difficult due to the formation of intermetallic phases. Machining has also proven difficult due to the rapid work hardening nature and the abrasiveness of the metal. In order to promote applications of nickel-titanium alloys in the medical device arena, processes to enhance site specific properties such as flexibility in a small region of a device must be developed.

SUMMARY OF THE INVENTION

The present invention relates to methods of treating linear elastic materials to produce localized areas of superelasticity. In an illustrative method in accordance with the present invention, a heat source such as a laser, induction coil, or infrared (IR) heater may be configured to selectively apply thermal energy to one or more localized areas on a linear elastic member to impart flexibility to the material. In certain exemplary methods, the heat source can be configured to heat the material beyond its final austenitic temperature $A_f$ to induce superelasticity and, in some cases, shape-memory to the material. In other exemplary methods, the heat source can be configured to selectively heat the material within a temperature range between the starting austenitic temperature $A_s$ and final austenitic temperature $A_f$ of the material to increase the recoverable strain. Medical devices such as embolic protection filters, vena cava filters, stents, and guidewires having localized areas of flexibility may be formed in accordance with the present invention.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
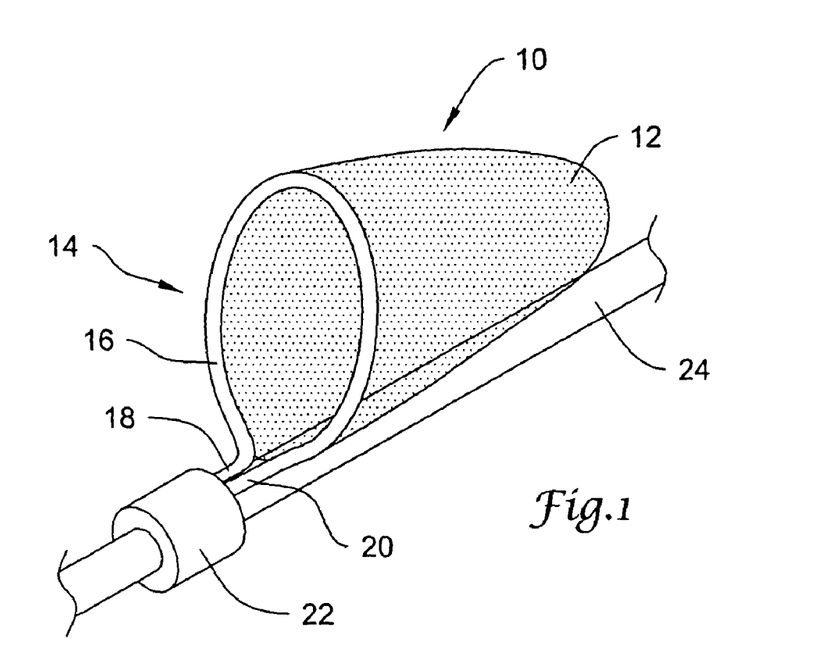
FIG. 1 is a perspective view of an illustrative embolic protection filter employing a wire loop formed of a linear elastic material.

FIG. 1 is a perspective view of an illustrative medical device 10 employing a linear elastic material. Medical device 10, illustratively an embolic protection filter, includes a filter membrane 12 coupled to a filter frame 14 or other support structure configured to support the filter membrane 12 in an expanded position within the body. Filter frame 14 includes a wire loop 16 forming a mouth of the filter that receives embolic debris contained in the blood stream. The ends 18,20 of the wire loop 16 can be attached via joint 22 to a guiding member 24 such as a guidewire or guide catheter that can be manipulated to position the device 10 within the body.

To impart greater axial and torsional stiffness to the filter frame 14, wire loop 16 may be formed from a linear elastic wire having a linear stress-strain response. The wire loop 16 may, for example, be formed of a linear elastic nickel-titanium alloy that has been cold-formed to impart a desired shape such as the loop structure depicted in FIG. 1. One example of a suitable linear elastic nickel-titanium alloy useful in forming the wire loop 16 is FHP-NT alloy, which is commercially available from the Furukawa Techno Material Company of Kangawa, Japan.

To facilitate placement and/or removal within the body, wire loop 16 may be configured to collapse into the lumen of a delivery catheter or sheath. In certain prior art designs such as that depicted in FIG. 2, an articulation region 26 formed by grinding away the outer layer of the linear elastic wire may be used to increase the flexibility of the wire loop 16. In use, the articulation region 26 acts as a hinge, permitting the wire loop 16 to bend or fold when radially collapsed within the delivery device.

Figure 2:
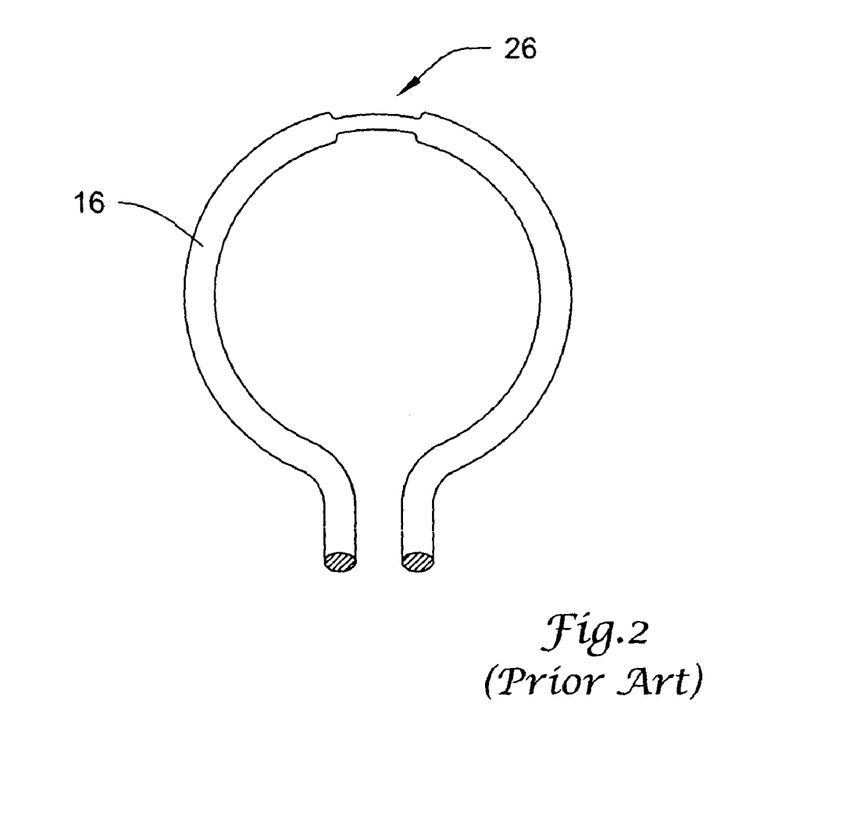
FIG. 2 is a perspective view of a prior art wire loop having a ground articulation region.

In certain processing applications, special tools may be required to finely grind the linear elastic wire member at the articulation region 26, adding to the cost and manufacturing steps necessary to form the device 10. For instance, a diamond grinding wheel or other suitable grinding device may be required to provide sufficient abrasion when grinding the material. Moreover, heating caused from the grinding process may, in certain situations, alter the mechanical properties of the material surrounding the articulation region 26.

Figure 3:
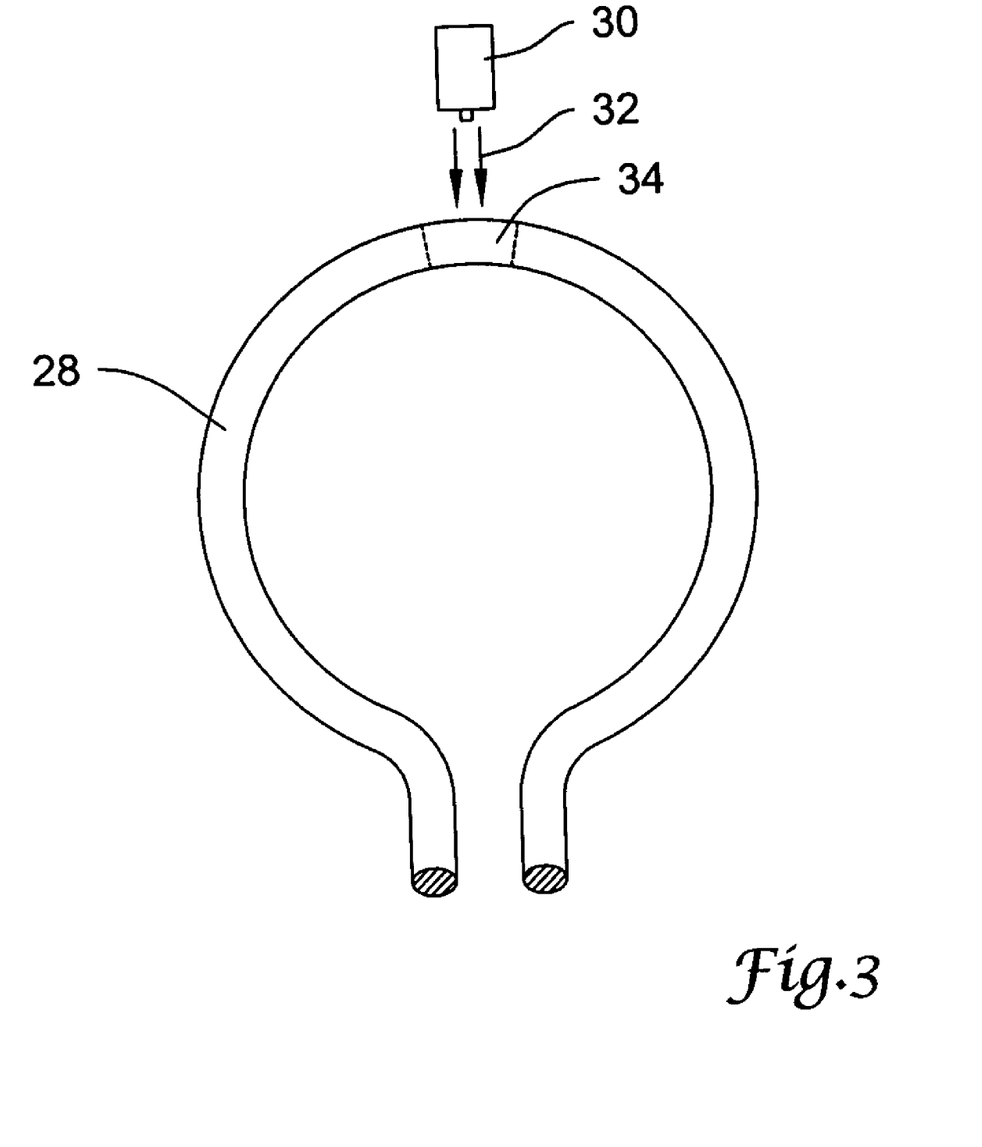
FIG. 3 is a perspective view of a linear elastic wire loop having a superelastic articulation region formed by selectively heat-treating a portion of the wire loop.

Referring now to FIG. 3, a linear elastic wire loop 28 having a superelastic articulation region formed in accordance with the present invention will now be described. Wire loop 28 may comprise a linear elastic wire member formed by cold-working or other suitable low-temperature process to impart a desired shape to the member, similar to that described above with respect to FIG. 2.

The wire member 28 may be formed from any number of suitable linear elastic materials. In addition to nickel-titanium alloys, other suitable materials may include, for example, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc (Cu—Zn), copper-zinc-aluminum (Cu—Zn—Al), copper-zinc-tin (Cu—Zn—Sn), copper-zinc-silicon (Cu—Zn—Si), iron-beryllium (Fe—Be), iron-nickel-titanium-cobalt (Fe—Ni—Ti—Co), iron-platinum (Fe—Pt), indium-thallium (In—Ti), iron-manganese (Fe—Mn), nickel-titanium-cobalt (Ni—Ti—Co), and copper-tin (Cu—Sn). In certain applications, the wire member 28 may be combined with other materials such as stainless steel, platinum, titanium, etc. to form a composite material exhibiting certain desirable characteristics within the body. For example, in certain applications the linear elastic material may be joined together with a relatively radiopaque material such as platinum (Pt) to increase the radiopacity of the composite member, allowing the device to be viewed with the aid of a fluoroscope.

In another aspect of the present invention, a heat source 30 may be employed to selectively heat-treat localized areas of the wire loop 28, inducing a superelastic response in the material. In one exemplary process, heat source 30 may comprise a laser configured to direct thermal energy 32 about the outer periphery of the linear elastic wire member 28 at location 34. The heat source 30 may be configured to heat the material at temperatures greater than the final austenitic temperature $A_f$ of the material to impart superelasticity and, in some cases, shape-memory to the material. As with the articulation region 26 described above with respect to FIG. 2, the selective application of heat about the outer periphery of the linear elastic wire member 28 may form an area of flexibility, which, in use, facilitates bending or folding of the wire loop 28 within the lumen of the delivery device.

In one exemplary process, the heat source 30 may be configured to selectively heat the wire member 28 to a temperature in the range of about 300 to 400° C., and more specifically about 325 to 375° C., corresponding to the temperature range at which the response of a linear elastic material transforms to a superelastic response. The precise temperature range at which the material transforms will, however, depend on a number of factors. In processes using nickel-titanium alloy, for example, the time required to treat the material may vary from 5-60 minutes, although other durations have been found to impact the response of the material.

In addition to the use of a laser heat source, other suitable heating sources may be utilized to thermally treat the material. Examples of other suitable heating techniques include for example electron beam/plasma heating, infrared (IR) heating, RF heating, to name a few. In one exemplary process, the linear elastic member may be heat-treated using an induction heating process. An induction coil or other suitable element may be placed about selective areas of the member where greater flexibility is desired. An applied AC current through the induction coil can be used to produce a magnetic field within the coil. As the member is inserted into the induction coil, eddy currents are induced within the member resulting in localized areas of heat. The precise depth at which the heating penetrates the member may be controlled by adjusting the amount and/or frequency of current applied to the induction coil, the amount of time the wire is subjected to heating, or the dimensions of the induction coil.

The process of selectively heating various regions of the linear elastic member may be accomplished at any stage of forming the medical device. Thus, although the heating step depicted in FIG. 3 is performed after the wire member 28 is shaped, it should be understood that such heating may occur at other stages of the manufacturing process. In certain applications, for example, the wire member 28 may be selectively heat-treated prior to the shaping process.

Figure 4:
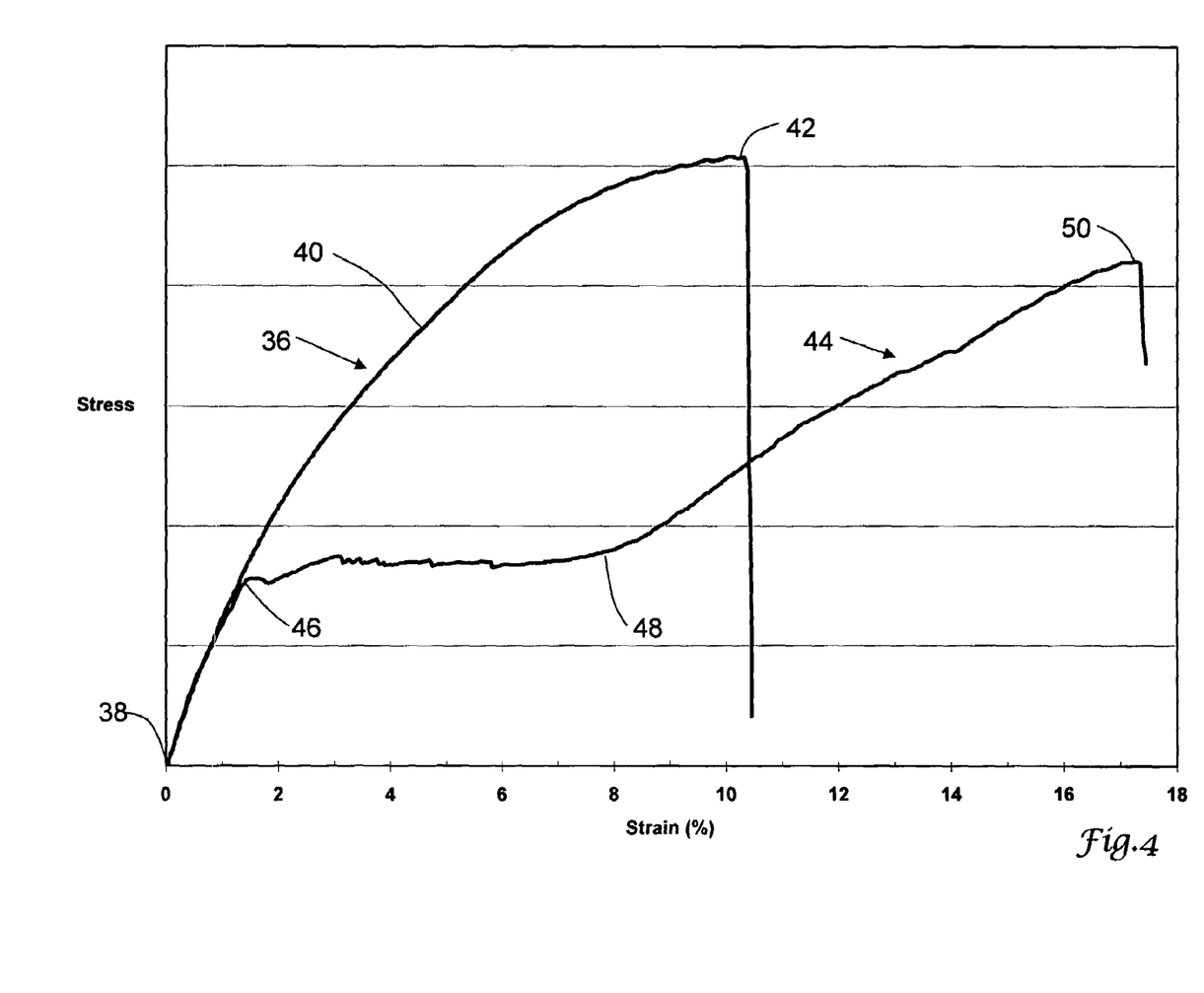
FIG. 4 is a graph of stress as a function of strain for treated and untreated linear elastic members subjected to a tensile force.

FIG. 4 is an exemplary graph of stress as a function of strain showing the response of identically configured linear elastic wires subjected to an applied tensile force. As shown in FIG. 4, a first curve 36 representing the stress-strain relationship of an untreated linear elastic wire member prior to treatment exhibits a relatively linear response from point 38 to point 40. At point 40, the linear elastic material begins to plastically deform until point 42, when the member reaches its ultimate tensile strength and critically fails. As can be seen from curve 36, the untreated linear elastic material exhibits a relatively linear stress-strain response.

As can be further seen in FIG. 4, a second curve 44 represents the response of a treated linear elastic member subjected to heat-treating, as described herein. As the treated linear elastic member is subjected to an applied tensile force, a relatively linear response is noted between points 38 and 46, similar to that exhibited by the untreated linear elastic member. However, at point 46, the treated member reaches a relatively constant stress plateau. At point 48, corresponding to a strain of about 8%, the stress in the material continues to increase until the material reaches its ultimate tensile strength at point 50. As can be seen by comparing curve 44 with curve 36, for strains greater than about 1%, the treated linear elastic member exhibits greater flexibility in comparison to the untreated linear elastic member. Furthermore, the treated linear elastic member is capable of enduring greater strains than the untreated linear elastic member before reaching critical failure.

While it is contemplated that the linear elastic material be heated to a temperature above the final austenitic temperature $A_f$ of the material in most applications, in some applications it may be desirable to treat the material at temperatures below $A_f$, but above the starting austenitic temperature $A_s$ of the material. For example, in applications utilizing linear elastic nickel-titanium alloy, some superelastic response may be imparted to selective regions of the member by heating the material to a temperature in the range of about 325-375° C., which corresponds generally to the temperature range at which the material transitions from a martensitic phase to an austenitic phase. By selectively heating the material within this temperature range, varying degrees of elasticity may be imparted to the wire member, as desired.

In addition to forming areas of flexibility on embolic protection filters, the aforesaid process may be useful to impart superelasticity and/or shape-memory to a variety of other medical devices. The selective heat-treatment of linear elastic materials may be useful for producing areas of flexibility on medical devices employing; for example, wires, tubes, ribbons, shafts, braids, needles, hooks, or other such components. Variations in the processing steps may be made depending on the amount of flexibility desired, the dimensions of the workpiece, or other desired characteristics.

Figure 5:
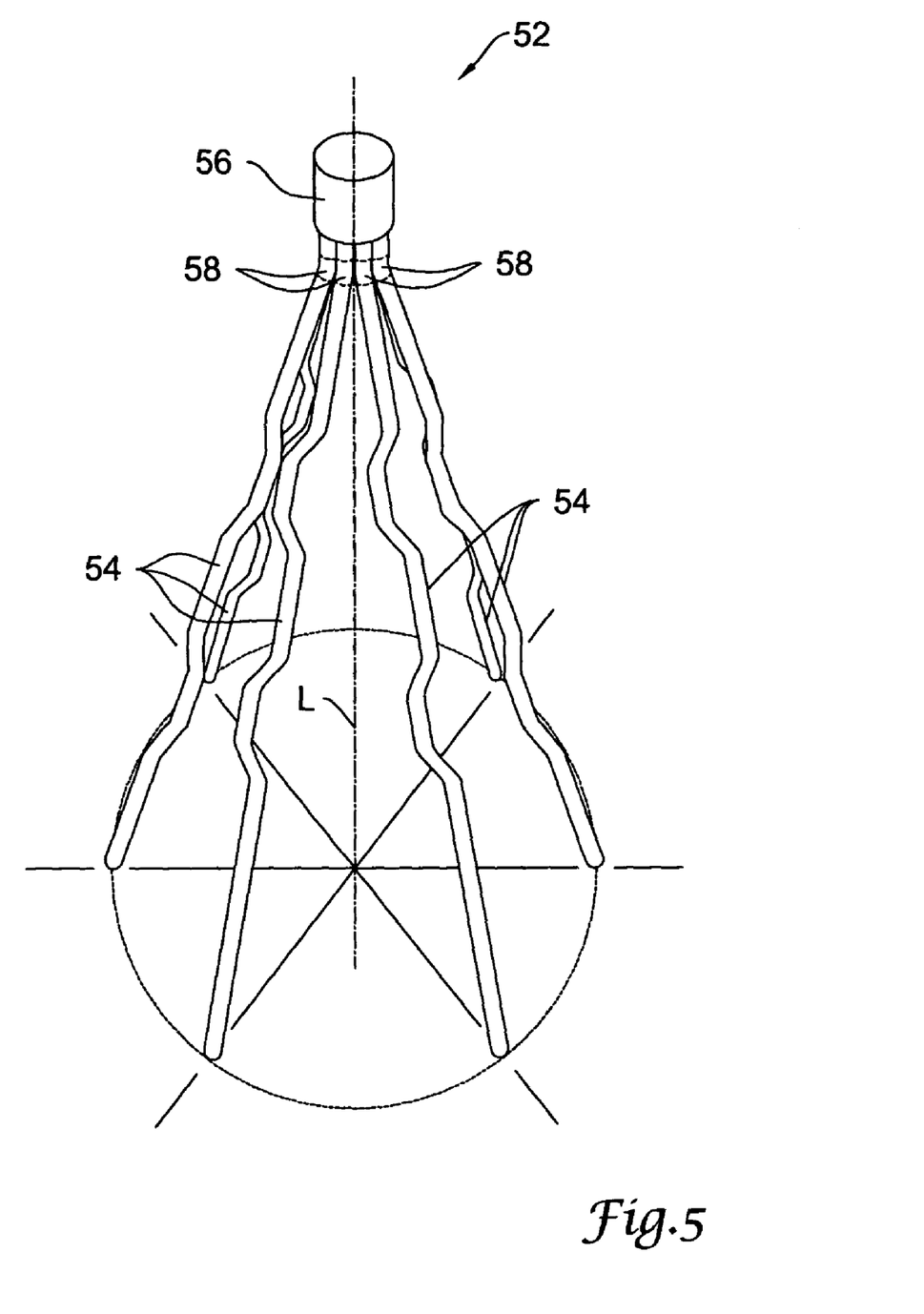
FIG. 5 is a perspective view of a vena cava filter employing a number of linear elastic filter legs each having a flexibility region formed by selectively heat-treating a portion of the filter legs.

In one such application illustrated in FIG. 5, a method of selectively heat-treating a linear elastic material in accordance with the present invention may used to impart flexibility to the filter legs of a vena cava filter. As shown in FIG. 5, a vena cava filter 52 may include a plurality of elongated filter legs 54 each coupled together at one end to an apical head 56. Each of the filter legs 54 may be biased to radially expand from a substantially straight position when collapsed within the lumen of a delivery catheter or sheath to an outswept, conical-shaped position when deployed in a blood vessel such as the inferior vena cava.

During deployment of the filter 52 within the body, it may be desirable to form a flexibility region on each of the filter legs 54 at or near the location where the filter legs 54 connect to the apical head 56. As described herein, a heat source (not shown) may be positioned adjacent to each filter leg 54 at location 58, indicated generally by dashed lines. The filter legs 54 may include a linear elastic material formed by a suitable low-temperature process to maintain the stiffness characteristics of the material. The heat source can then be activated to selectively apply thermal energy at location 58 to form a superelastic bending joint on each filter leg 54.

In certain embodiments, it may also be desirable to impart shape-memory to the filter leg 54. For instance, it may be desirable to configure location 58 of each filter leg 54 to bend from a relatively straight configuration to a bent configuration when exposed to a particular temperature such as body temperature (37° C.).

Figure 6:
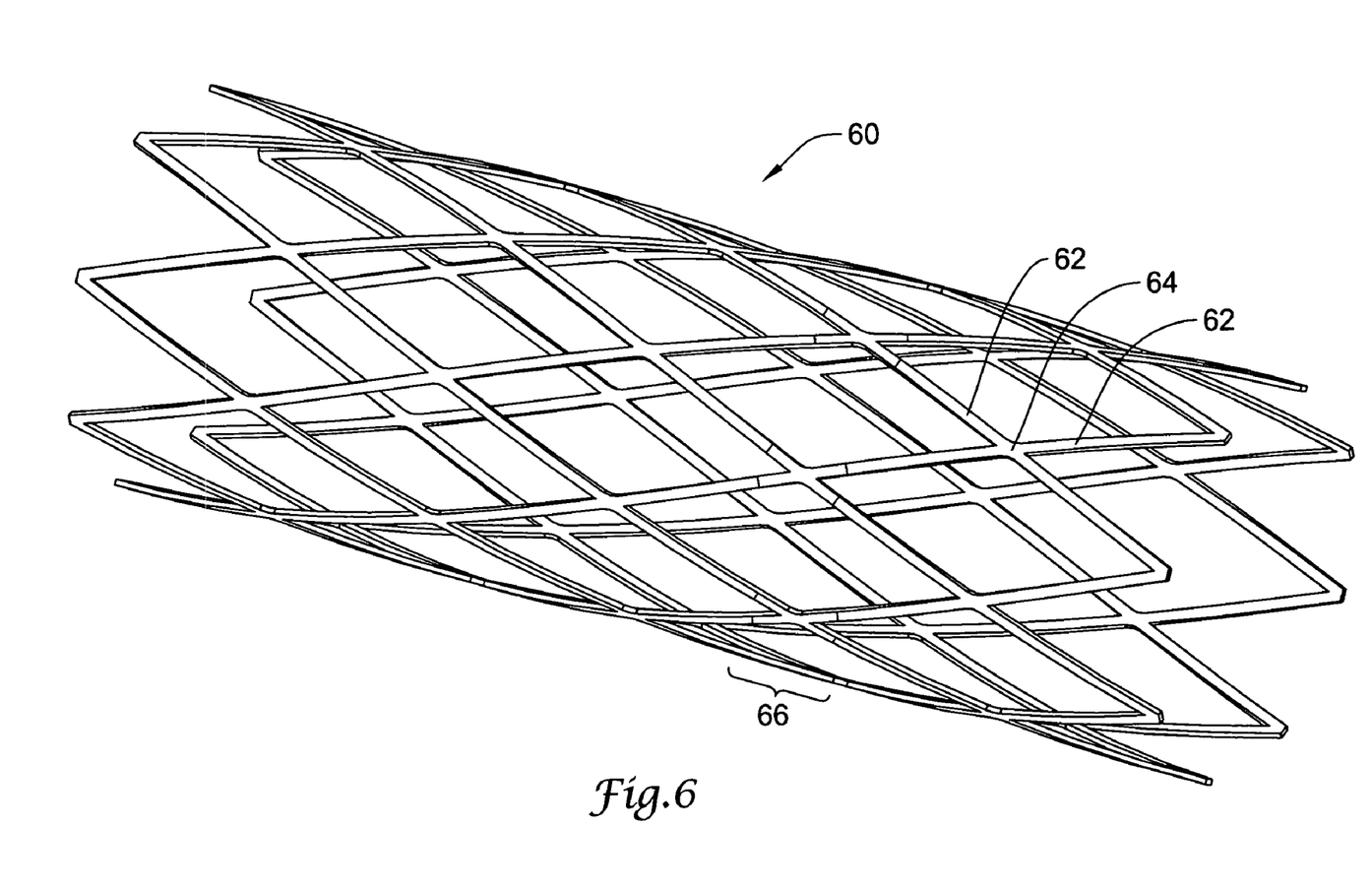
FIG. 6 is a perspective view of a stent having a flexibility region formed by selectively heat-treating a portion of the stent.

In another exemplary application illustrated in FIG. 6, a method of selectively heat-treating a linear elastic material in accordance with the present invention may be used to impart flexibility to particular areas of a stent. Stent 60, illustratively a vascular stent, may be formed from a linear elastic workpiece having certain desired stiffness characteristics. The stent 60 may include a number of strands 62 and interconnecting nodes 64 formed, for example, by chemical etching or laser cutting a single sheet of linear elastic material, and then forming the member into a desired shape such as a tube. The formation of the strands 62 and nodes 64 may be accomplished in a manner that preserves the stiffness and response characteristics of the material.

In certain applications it may be desirable to impart flexibility to each of the strands 62 and/or nodes 64 to permit the stent 60 to be radially collapsed within the lumen of a delivery device during placement. In other applications, it may be desirable to impart flexibility to selective regions of the stent 60 to permit the device to be placed in certain anatomies such as a curved blood vessel. For example, as indicated by dashed lines in FIG. 6, a bending region 66 may be formed circumferentially about the stent 60 by selectively heating certain strands 62 and/or nodes 64 at various locations along the length of the stent 60.

Figure 7:
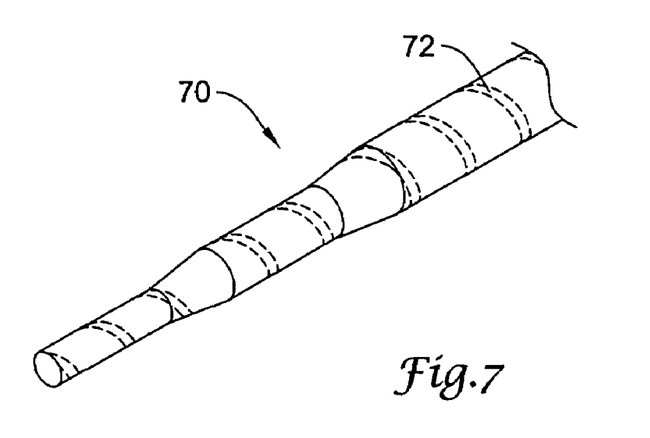
FIG. 7 is a perspective view of a core wire having a spiraled flexibility region formed by selectively heat-treating a portion of the core wire.

In another exemplary application illustrated in FIG. 7, a method of selectively heat-treating a linear elastic material in accordance with the present invention may be used to impart a spiral, braid or other desired pattern to an elongated member such as a guidewire or guide catheter. As shown in FIG. 7, a tapered core wire 70 used in the construction of a guidewire may include a linear elastic material that has been selectively heat-treated to form a spiraled flexibility region 72 about the outer periphery of the member. The spiraled flexibility region 72 may be formed by heat-treating localized areas of the core wire 70 at temperatures above the final austenitic temperature $A_f$ of the material, or by heat-treating at temperatures below the final austenitic temperature $A_f$ but above the starting austenitic temperature $A_s$ of the material. In use, the spiraled flexibility region 72 increases the flexibility of the core wire 70 while maintaining the pushability, kink resistance, and torqueability characteristics desired in the member.

Figure 8:
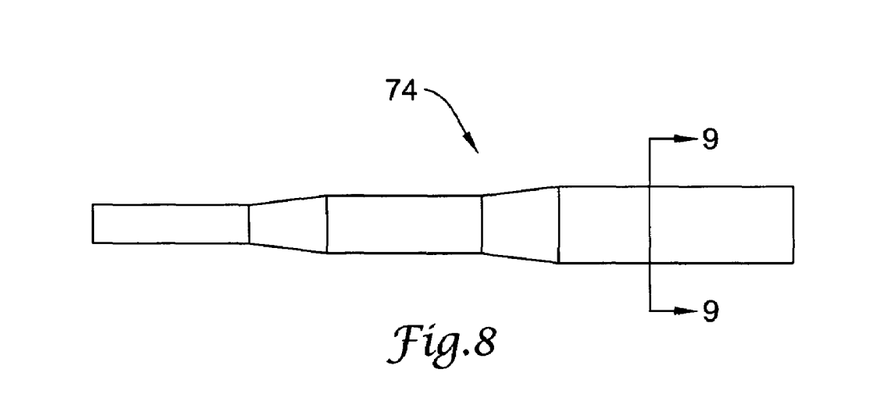
FIG. 8 is a side view of a portion of a core wire having a composite structure formed by selectively heat-treating the outer portion of the core wire.
Figure 9:
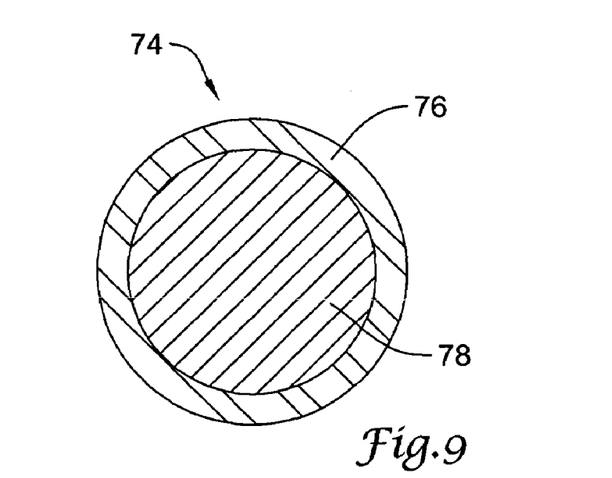
FIG. 9 is a cross-sectional view along line 9-9 of FIG. 8, showing the composite structure of the core wire.

In another exemplary application illustrated in FIGS. 8-9, the entire outer surface of the core wire may be thermally treated to form a flexible outer region along the length of the core wire. Using, for example, an induction-heating process, a tapered core wire member 74 formed of a linear elastic material may be thermally treated along its entire length to form a composite structure with certain flexibility characteristics. As shown in FIG. 9, the core wire 74 can be selectively heat-treated to form a superelastic outer region 76 while maintaining the linear response characteristics of the material along the inner region 78 of the core wire 74.

Although filters, stents and guidewires are specifically illustrated in the various Figures, it should be understood that other medical devices may be manufactured from linear elastic materials processed in accordance with the steps described herein. Examples of other suitable medical devices include guide catheters, stent connectors, embolectomy devices, baskets, snares, stiffening wires, guidewire coils, guidewire extensions, and bone anchors.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size, and arrangement of parts without exceeding the scope of the invention.

What is claimed is:

1. An embolic protection filter, comprising:
   an elongate shaft;

a filter coupled to the shaft, the filter including a filter loop and a filter membrane coupled to the filter loop;

wherein the filter loop includes a nickel-titanium alloy; and wherein the filter loop includes a first portion that includes a linear elastic nickel-titanium alloy and wherein at least one localized area of flexibility is defined in the filter loop by selectively heating an intermediate portion of the filter loop to a temperature sufficient to induce superelasticity in the filter loop and define a super elastic nickel-titanium alloy second portion of the filter loop.

2. An embolic protection filter, comprising:

an elongate shaft;

a filter coupled to the shaft, the filter including a linear elastic member having a linear elastic region and a localized superelastic region;

wherein the localized superelastic region is formed by heating an intermediate portion of the linear elastic member to a temperature sufficient to form the localized superelastic region within the linear elastic member, wherein the linear elastic member defines a filter leg.

3. The medical device of claim 2, wherein the linear elastic member has only one localized superelastic region.

4. The medical device of claim 2, wherein the localized superelastic region comprises an articulation region.

5. The medical device of claim 2, wherein the localized superelastic region is formed by heating to a temperature that is at least as high as a final austenitic temperature of a material forming the linear elastic member.

6. The medical device of claim 2, wherein the linear elastic member is formed of a linear elastic nickel-titanium alloy and the localized superelastic region comprises, after the heating step, a superelastic nickel-titanium alloy.

* * * * *